United States Patent
Sakamoto et al.

(10) Patent No.: US 6,787,001 B2
(45) Date of Patent: Sep. 7, 2004

(54) METHOD FOR DISTILLING (METH) ACRYLIC ACID SOLUTION

(75) Inventors: Kazuhiko Sakamoto, Himeji (JP); Sei Nakahara, Himeji (JP); Yukihiro Matsumoto, Kobe (JP); Kenji Sanada, Himeji (JP); Masatoshi Ueoka, Himeji (JP)

(73) Assignee: Nippon Shokubai Co. Ltd., Osaka (JP)

( * ) Notice: Subject to any disclaimer, the term of this patent is extended or adjusted under 35 U.S.C. 154(b) by 0 days.

(21) Appl. No.: 10/086,931

(22) Filed: Mar. 1, 2002

(65) Prior Publication Data

US 2002/0134660 A1 Sep. 26, 2002

(30) Foreign Application Priority Data

Mar. 21, 2001 (JP) ......................................... 2001-080075

(51) Int. Cl.$^7$ .............................. B01D 3/36; B01D 3/42; C07C 51/44; C07C 57/04
(52) U.S. Cl. .................. 203/2; 203/49; 203/60; 203/62; 203/69; 203/70; 203/95; 203/DIG. 9; 203/DIG. 21; 562/600
(58) Field of Search .......................... 203/1–3, 49, 60, 203/62, 69, 70, 95, DIG. 9, DIG. 21, 8, 100; 562/600

(56) References Cited

U.S. PATENT DOCUMENTS

| 4,021,310 A |   | 5/1977  | Shimizu et al. |
| 4,554,054 A | * | 11/1985 | Coyle ........................... 203/15 |
| 4,987,252 A | * | 1/1991  | Kuragano et al. .......... 562/600 |
| 5,132,918 A | * | 7/1992  | Funk ........................... 700/270 |
| 5,315,037 A |   | 5/1994  | Sakamoto et al. |

FOREIGN PATENT DOCUMENTS

| EP | 0009545    | * | 4/1980 |
| JP | 122327     | * | 9/1981 |
| JP | 8052-239   | * | 3/1983 |
| JP | A-8-3099   |   | 1/1996 |
| JP | A-10-120618|   | 5/1998 |

\* cited by examiner

*Primary Examiner*—Virginia Manoharan
(74) *Attorney, Agent, or Firm*—Mathews, Collins, Shepherd & McKay, P.A.

(57) ABSTRACT

A method for distilling a raw material liquid containing (meth)acrylic acid substantially free from azeotropic solvents, collected with a collection agent from a mixed gas obtained by gas phase catalytic oxidation reactions which includes feeding to a distillation column the raw material liquid which temperature is substantially equal to that of the entrance place in the column.

18 Claims, No Drawings

METHOD FOR DISTILLING (METH) ACRYLIC ACID SOLUTION

BACKGROUND OF THE INVENTION

1. Field of the Invention

The present invention relates to a method for distilling (meth)acrylic acid.

2. Description of Related Art

Acrylic acid is generally produced by subjecting gas phase catalytic oxidation reaction of propylene and/or acrolein with a molecular oxygen-containing gas, contacting a resulting acrylic acid-containing gas with water to collect as an aqueous acrylic acid solution, and separating and collecting acrylic acid from the acrylic acid solution. In the acrylic acid-containing gas, there are contained by-products such as acetic acid, formic acid, acetaldehyde, formaldehyde or the like. Among them, acetic acid is contained in relatively higher amount. In order to produce acrylic acid in a high purity, it is necessary to remove acetic acid therefrom. When acetic acid therein is intended to remove by means of distillation, the distillation temperature become higher (Boiling point of acetic acid: 118.1° C.), thereby acrylic acid is liable to polymerize. Since acrylic acid and acetic acid have small relative volatilities, there is the problem that it is difficult to remove acetic acid from the acrylic acid solution by simple distillation.

Then, in the above collecting step, the aqueous acrylic acid solution is fed to an azeotropic separation column to be distilled (azeotropic dehydration method) in order to separate and collect acrylic acid in a high purity from the aqueous acrylic acid solution, i.e., to collect a high purity of acrylic acid substantially free from acetic acid and water by separating acrylic acid from the acetic acid and water. In the azeotropic separation column, distillation is performed in the presence of azeotropic solvents, an azeotropic mixture of acetic acid, water and the azeotropic solvent distilled from the top thereof, and acrylic acid obtained from the bottom thereof. Impurities having a low boiling point, other than acetic acid and water, can be readily removed from the solution because of their low boiling points. Thus, such impurities do not need azeotropic distillation.

However, in the above azeotropic separation column, the acrylic acid is liable to polymerize since many ingredients are present in the solution. The produced acrylic acid polymer accumulates in the column, therefore it is difficult for the azeotropic distillation column to be operated for a long period of time.

There are proposed lots of polymerization inhibitors so as to prevent the polymerization of acrylic acid. For example, U.S. Pat. No. 4,021,310 describes a polymerization inhibitor of at least one selected from the group consisting of hydroquinone, methoquinone (p-methoxyphenol), cresol, phenol, t-butylcatechol, diphenylamine, phenothiazine, and methylene blue; at least one selected from the group consisting of copper dimethyldithiocarbamate, copper diethyldithiocarbamate, and copper dibutyldithiocarbamate; and a molecular oxygen.

As a result of our research, we have found that the polymerization of acrylic acid cannot be fully prevented even if such polymerization inhibitor has been adopted. When the inhibitor is used in a prescribed amount, it does not provide full prevention effects, and there are occurred popcorn polymer and viscous polymer during distillation, thereby the continuous operation of acrylic acid production equipments including the azeotropic distillation column become impossible. Large amount of the inhibitor may be used so as to fully prevent the polymerization, but the use of the large amounts leads economical disadvantage as well as there occurred the problems of apparatus corrosion and waste water treatment. As a result, its practical use could be difficult.

The problem of polymerization in the azeotropic separation column as mentioned above is also found in the method for producing methacrylic acid by subjecting gas phase catalytic oxidation reaction of at least one selected from the group consisting of isobutylene, t-butyl alcohol and methacrolein with a molecular oxygen-containing gas.

Azeotropic separation procedure will be further explained. U.S. Pat. No. 5,315,037 describes a method for collecting a purified acrylic acid employing a distillation column as the azeotropic column in which an aqueous acrylic acid solution is azeotropically performed to distill a mixture consisting essentially of acetic acid, water, and the azeotropic solvent from the top thereof, and to collect a purified acrylic acid substantially free from acetic acid, water, and the azeotropic solvent from the bottom thereof. In addition, JP-A-10-120,618 describes a method for producing a purified acrylic acid using two distillation columns, such as an azeotropic dehydration and acetic acid separation columns, in which the bottom liquid of the azeotropic dehydration column is led to the acetic acid separation column wherein distillation is performed again to remove acetic acid. In this method, the bottom liquid of azeotropic dehydration column is cooled and then led to such an acetic acid separation column so as to heighten the separation efficiency of the acetic acid therein. However, this method relates to techniques for purifications of solutions containing acetic acid, acrylic acid, and azeotropic solvents, but does not describe prevention of polymerization in the case of distillation of (meth)acrylic acid solutions substantially free from azeotropic solvents. In addition, the solution includes the azeotropic agents, so that the concentration of (meth) acrylic acid therein becomes lowered. The method does not describe prevention of polymerization in the solutions containing higher concentration of (meth)acrylic acid.

Effects of prevention of polymerization have not been fully solved by the above methods, and it is desired to distill the above-mentioned solution of polymerizable (meth) acrylic acid for a long period of time.

In addition to the azeotropic distillation column, there can be cited, as columns wherein polymerization is liable, an aldehyde distillation column in which the aldehyde treating agent is added to the (meth)acrylic acid solution, and then the resultant is distilled to obtain a purified acrylic acid; distillation column for separating materials having high boiling points in which a purified acrylic acid is obtained from the top thereof by removing impurities having high boiling points from the (meth)acrylic acid solution or the like. The aldehyde treating agent such as hydrazine hydrate is used in the aldehyde distillation column, and acrylic acid is liable to polymerize in the distillation columns in the presence of the aldehyde treating agent and a product of aldehyde and the aldehyde treating agent.

JP-A-8-3,099 describes a method for preventing the polymerization of (meth)acrylic acid during distillation in the presence of an aldehyde treating agent using a composition for preventing polymerization comprising a p-phenylenediamine compound, phenol compound, and phenothiazine.

In the distillation column for separating materials having high boiling points, (meth)acrylic acid is liable to polymerize since the acid is exposed to high temperatures.

SUMMARY OF THE INVENTION

An object of the present invention is to provide a method for distilling a raw material liquid containing (meth)acrylic acid substantially free from azeotropic solvents for effectively preventing the polymerization of (meth)acrylic acid during distillation and for performing distillation for a long period of time in the production of (meth)acrylic acid.

As a result of our research, we have found that (i) A (meth)acrylic acid solution from a collection column for (meth)acrylic acid is generally exposed to air for the time being, then fed to a distillation column or tower set at a prescribed temperature. A temperature difference is present between (meth)acrylic acid solution as the raw material and the entrance place, at which the raw material liquid enters, in the distillation column. When the temperature difference is high, there is occurred partial condensation or drift flow of the (meth)acrylic acid solution in the column, and polymerization is liable to occur.

(ii) The temperature of (meth)acrylic acid solution from the collection column for (meth)acrylic acid is generally dispersed. When the (meth)acrylic acid solution is stored in an intermediary tank for the time being and then fed to the column, the temperature thereof is also dispersed if the amount of piling liquids is not fixed. In such a case, polymerization of (meth)acrylic acid is liable to occur in distillation columns such as a distillation column for separating (meth)acrylic acid and the collecting solvent, aldehyde distillation column, and distillation column for separating high boiling materials.

We have found that in performing distillation, polymerization in the above column can be prevented and distillation can be stably performed for a long period of time by feeding the raw materials containing (meth)acrylic acid substantially free from azeotropic solvents which temperature is substantially equal to that of the entrance place in the distillation column to the distillation column, and finally completed the present invention.

The present invention relates to a method for distilling a raw material liquid containing (meth)acrylic acid substantially free from azeotropic solvents, collected with a collection agent from a mixed gas obtained by gas phase catalytic oxidation reactions characterized by feeding to a distillation column the raw material liquid which temperature is substantially equal to that of the entrance place in the column.

According to the present method, it can effectively prevent polymerization in each distillation column in the case of recovering (meth)acrylic acid from the (meth)acrylic acid solution substantially free from azeotropic solvents. With this procedure, a production device including the distillation column can be stably operated for a long period of time.

The above and other objects, features and advantages of the present invention will become clear from the following description of the preferred embodiments.

DETAILED DESCRIPTION OF THE PREFERRED EMBODIMENTS

A mixed gas is fed to a collection column for (meth) acrylic acid wherein (meth)acrylic acid is collected with a collection agent, the mixed gas being produced for example by gas phase catalytic oxidation reaction of propylene and/or acrolein with a molecular oxygen-containing gas or by gas phase catalytic oxidation reaction of at least one member selected from the group consisting of isobutylene, t-butyl alcohol and methacrolein with a molecular oxygen-containing gas.

This step will be explained as follows.

The step is not restricted when (meth)acrylic acid is obtained by gas phase catalytic oxidation reaction but for example acrylic acid may be produced by a conventional manner as follows.

Propylene and/or acrolein are allowed to partially oxidize with a molecular oxygen-containing gas, such as oxygen and air or the like, in the presence of a known catalyst. Generally, oxidation reaction is performed in a two-step procedure. The first catalyst is capable of oxidizing a raw material gas containing propylene to form mainly acrolein, and then the second catalyst is capable of oxidizing a raw material gas containing the resultant acrolein to form mainly acrylic acid. The first catalyst may contain complex oxides of iron, molybdenum and bismuth, and the second catalyst may contain vanadium at essential component. The oxidation reaction may be performed in the temperature range of 250° C. to 380° C.

The mixed gas obtained by the gas phase catalytic oxidation reaction may contain acrylic acid, a molecular oxygen-containing gas, and unreacted raw materials, as well as impurities such as byproduced water, acetic acid, propionic acid, maleic acid, acetone, acrolein, furfural, formaldehyde or the like.

The mixed gas is contacted with a collection agent so as to collect acrylic acid from the mixed gas. The collection agent is not restricted if it can absorb or dissolve acrylic acid but may include an organic compound such as diphenyl ether, diphenyl, and mixtures thereof; water and a process waste water. By the term "process waste water" as used herein, is meant a wastewater exhausted from acrylic acid production process. The process wastewater may include water distilled away from an azeotropic dehydration distillation column and wastewater from ejector or the like. The resultant solution containing acrylic acid may be called to as acrylic acid solution.

Contact of the acrylic acid-containing mixed gas with the solvent may be performed by adopting any of the known methods, which are available for establishing the contact of the sort in question. As examples of the method usable herein, crossflow contacts using a bubble-cap tray, a uniflux tray, a sieve tray, a jet tray, a valve tray, a ventury tray, and an arbitrary combination thereof; and counterflow contacts using a turbo grid tray, a dual flow tray, a ripple tray, a kittel tray, a random packing, a structure packing, and an arbitrary combination thereof may be cited.

The acrylic acid solution obtained contains the aforementioned impurities in a small amount besides the acrylic acid. Acetone, acrolein, formaldehyde, etc., when necessary, may be removed by means of stripping or distillation.

To the acrylic acid solution, a polymerization inhibitor such as hydroquinone may be added, when necessary.

The acrylic acid solution obtained from the collection column for acrylic acid is fed to a distillation column wherein acrylic acid and the collection agent are azeotropically separated with an azeotropic solvent. In the case of two-column distillation, this distillation column corresponds to an azeotropic dehydration distillation column. Azeotropic agents include a known solvent to be used generally in these azeotropic distillations but for example may include, as described in U.S. Pat. No. 5,315,037, a mixed solvent of at least one selected from the group consisting of diethyl ketone, methyl propyl ketone, methyl isobutyl ketone, methyl-t-butyl ketone, and n-propyl acetate; at least one selected from the group consisting of toluene, heptane, and methylcyclohexane. The solvent may be used singly. Among them, toluene is preferred.

In the present invention the azeotropic solvent in the acrylic acid solution have to be removed by azeotropic dehydration distillation. A raw material liquid containing acrylic acid substantially free from azeotropic solvent which temperature is substantially equal to the entrance place in the distillation column is fed to the distillation column in recovering acrylic acid from the resultant acrylic acid solution by means of distillation. Here, the "substantially" in the "substantially free from" means that the concentration of azeotropic acids is not more than 0.1% by weight, and preferably not more than 0.05% by weight, based on the weight of raw material liquids, and the "substantially" in the "substantially equal" means to satisfy the condition (1).

According to the present method, the temperature of the raw material liquid is adjusted, when necessary, to fulfill the following condition (1) in the case of distilling acrylic acid solution, then the adjusted liquid is fed to the distillation column.

(1) The temperature difference, i.e., absolute value |T0–T1|, between the temperature of the raw material liquid to be fed (T0) and the temperature of the entrance place in the distillation column (T1) may be within 30° C., preferably within 20° C., and the most preferably within 10° C.

The temperature of the entrance place in the column may be readily measured employing a temperature meter. Distillation may be performed by a multistage distillation column, and therefore the temperature is measured on the column plate to which the raw material liquid is fed in the column, which temperature is called as to the temperature of the entrance place in the column. After the temperature of the entrance place has been measured, the raw material liquid to be fed may be heated or cooled when necessary so as to adjust the temperature of the raw material liquid thereto. This heating or cooling may be performed by a heat exchanger.

In the present invention, it is preferable to adjust the temperature difference within 30° C. together with to make the fluctuation range of temperature (T0) of the raw material liquid smaller. To put it concretely, it may adjust the fluctuation range to fulfill the following condition (2).

(2) The difference (t1–t2) between the maximum temperature of the raw material liquid (t1) and the minimum temperature thereof (t2), i.e., this is herein called as "the fluctuation range ($\Delta T0$) of temperature of the raw material liquid (T0)" may be within 10° C., preferably within 5° C., and especially within 3° C.

Polymerization can be effectively prevented in the distillation column by making the fluctuation range ($\Delta T0$) of temperature of the raw material liquid smaller. Further, both t1 and t2 should satisfy the condition (1) for temperature difference.

According to the preferred embodiment, the raw material liquid is when necessary adjusted to fulfill the following formulas $$0° C. \leq |T0-T1| \leq 30° C.,$$

$$0° C. \leq \Delta T0 \leq 10° C.,$$

in particular $$0° C. \leq |T0-T1| \leq 10° C.,$$

$$0° C. \leq \Delta T0 \leq 3° C.,$$

and then fed to the distillation column.

In addition to the above, it is preferred to make the temperature of raw material liquid (T0) smaller than the bottom temperature of the distillation column (T2). This is because when the raw material liquid having a higher temperature than the bottom temperature is fed to the column, a harder environment than the essential maximum temperature to be operated (the bottom temperature) is formed within the column, and the effects of the present invention cannot be exhibited to the highest possible extent.

Concentration of the subject in the raw material liquid, for example acrylic acid, may depend on purity of the products but for instance not less than 85% by weight, preferably 90 to approximately 100% by weight, and most preferably 95 to approximately 100% by weight.

Next, the present invention will be explained in more detail with reference to the aqueous acrylic acid solution. The distillation condition (steady state) in the azeotropic separation column of the aqueous acrylic acid solution is usually as follows:

Operation pressure: 150 to 250 hPa

Top temperature of the column: 45° C. to 55° C.

Temperature at which the aqueous acrylic acid solution is fed to the entrance place in the column: 60° C. to 90° C.

Azeotropic agent concentration in the raw material liquid: less than 0.1% by weight Bottom temperature: 100° C. to 110° C.

Reflux ratio: 0.1 to 1.6.

Hence, on the assumption that temperature of the entrance place is 80° C. and the bottom temperature is 100° C., the aqueous acrylic acid solution as the raw material is adjusted to a temperature of 50° C. to 110° C., preferably 60° C. to 100° C., especially 70° C. to 90° C., and then fed to the azeotropic separation column. Furthermore, the fluctuation range of temperature of the aqueous acrylic acid solution may be preferably adjusted within 10° C., more preferably within 50° C., and the most preferably within 3° C.

In the production process of acrylic acid, the aqueous acrylic acid solution as the raw material is stored in an intermediate tank for a while, and then often fed to the azeotropic separation column. In this case, since the temperature of the aqueous acrylic acid solution is in the neighborhood of normal temperature, acrylic acid becomes liable to polymerize if the acrylic acid solution is fed to the azeotropic separation column as it is. In contrast, in the present invention, adjusting temperature of the aqueous acrylic acid solution within the prescribed range by means of a heat exchanger or the like, and then feeding the resultant to the azeotropic separation column can effectively prevent polymerization.

Next, the present invention will be explained in more detail with reference to an aldehyde distillation column for separating the aldehyde from acrylic acid. An aldehyde treatment is usually performed for the raw material liquid containing acrylic acid, and preferably performed after the separation of acetic acid from the raw material liquid. The distillation condition (steady state) in the aldehyde distillation column is usually as follows:

Operation pressure: 10 to 300 hPa

Top temperature of the column: 45° C. to 95° C.

Temperature at which the raw material liquid is fed to the entrance place in the column: 45° C. to 100° C.

Acrylic acid concentration in the raw material liquid: 85 to approximately 100% by weight Azeotropic agent concentration in the raw material liquid: less than 0.1% by weight Bottom temperature: 50° C. to 100° C.

Reflux ratio: 0.1 to 1.0.

Hence, on the assumption that temperature of the entrance place is 60° C. and the bottom temperature is 62° C., the raw material liquid is adjusted to a temperature of 30° C. to 62° C., preferably 40° C. to 62° C., especially 50° C. to 62° C., and then fed to the aldehyde distillation column. Furthermore, the fluctuation range of temperature of the raw material liquid maybe preferably adjusted within 10° C., more preferably within 5° C., and the most preferably within 3° C.

Lastly, the present invention will be explained in more detail with reference to a distillation column for separating high boiling point materials. Here, the high boiling point material means a compound having a higher boiling point temperature than that of the purified material, such as maleic acid in the case of acrylic acid. Separating high boiling point materials is usually performed for the raw material liquid containing acrylic acid, and preferably performed after the separation of acetic acid from the raw material liquid and/or the distillation for separating aldehydes in the column. The distillation condition (steady state) in the distillation column is usually as follows:

Operation pressure: 10 to 400 hPa

Top temperature of the column: 45° C. to 110° C.

Temperature at which the raw material liquid is fed to the entrance place in the column: 50° C. to 120° C.

Acrylic acid concentration in the raw material liquid: 85 to approximately 100% by weight Azeotropic agent concentration in the raw material liquid: less than 0.1% by weight Bottom temperature: 70° C. to 190° C.

Reflux ratio: 0.5 to 5.

Hence, on the assumption that temperature of the entrance place is 80° C. and the bottom temperature is 90° C., the raw material liquid is adjusted to a temperature of 50° C. to 90° C., preferably 60° C. to 90° C., especially 70° C. to 90° C., and then fed to the distillation column. Furthermore, the fluctuation range of temperature of the raw material liquid may be preferably adjusted within 10° C., more preferably within 5° C., and the most preferably within 3° C.

In the above each distillation column, the raw material liquid may be introduced to an entrance place or two or more entrance places of the distillation column. As the divisional methods, there are cited two methods, one relates to around the distillation column and the other relates to the top and bottom direction thereof. In these cases, the raw material liquid is adjusted in temperature to fulfill the above condition (1) or conditions (1) and (2), and then fed to the distillation column.

EXAMPLES

The present invention will be explained in more detail with reference to the examples, but not restricted with these examples.

EXAMPLE 1

An aqueous acrylic acid solution is subjected to continuous operation of azeotropic separation using a distillation column having an inner diameter of 105 mm. In the column, 50 stages of sieve trays made of stainless steel were interpolated at intervals of 147 mm there into, at the top part, a tube for distilled, tube for feeding reflux liquid and tube for feeding polymerization inhibition solution equipped, at the intermediate part, i.e., the 26th stage, a tube for feeding a raw material liquid equipped, and at the bottom part, a can, tube for withdrawing the bottom liquid and tube for supplying oxygen equipped.

Azeotropic separation operation was performed under the conditions that the raw material liquid was an aqueous acrylic acid solution containing 66.5 wt. % of acrylic acid, 30 wt. % of water and 2.5 wt. % of acetic acid (the azeotropic solvent: not more than 1 ppm, which is a detectable limit), which had been produced by the gas phase catalytic oxidation reaction of propylene (a first catalyst: $Co_4Fe_1Bi_1W_2Mo_{10}Si_{1.35}K_{0.06}$ except for oxygen, a second catalyst: $Mo_{12}V_{4.6}Cu_{2.2}Cr_{0.6}W_{2.4}$ except for oxygen, and a raw material gas: 5.5 vol. % of propylene, 5.0 vol. % of steam, and 7.7 vol. % of oxygen, the molar ratio of oxygen to propylene: 1.4) (see JP-B-60-32615, which is incorporated by reference in its entirety.), toluene was used as the azeotropic solvent, operation pressure 170 hPa, the top temperature 50° C., the temperature at the 26th stage 75° C., the bottom temperature 100° C., the reflux ratio (total mole of reflux liquid per unit time/total mole of distilled liquid per unit time) 1.35, and the amount of supplying raw material liquid 8.5 liter/hr. In this case, the raw material liquid was maintained at a temperature of 70±1° C., and fed to the column.

A 10 ppm of copper dibutyldithiocarbamate, and 100 ppm of phenothiazine in toluene, and 100 ppm of hydroquinone in water (each based on the amount of evaporated vapor of acrylic acid) as the polymerization inhibitor were fed to the top part of the column. Furthermore, oxygen gas was fed to the bottom part thereof at 0.3% of volume based on the amount of evaporated vapor of acrylic acid.

The composition of the withdrawn bottom liquid in a steady state contained 97 wt. % of acrylic acid, 0.03 wt. % of acetic acid, 0.02 wt. % of water, 0.001 wt. % of toluene, and 2.95 wt. % of residue. Further, the distilled oil was recycled as the reflux liquid.

Continuous operation was steadily performed for 30 days under the above conditions. After stopped, when the interior of the column was inspected with his eyes, there was found no occurrence of polymer.

EXAMPLE 2

The procedure of Example 1 was repeated, except that the raw material liquid was fed to the column on the condition that the temperature of the raw material liquid to be fed was allowed to disperse in the range of 60° C. to 80° C. (70±10° C.).

Continuous operation was steadily performed for 30 days under the above conditions. After stopped, when the interior of the column was inspected with his eyes, there was found occurrence of little polymer.

COMPARATIVE EXAMPLE 1

The procedure of Example 1 was repeated, except that the raw material liquid keeping a temperature of 25±1° C. was fed to the column.

When operation was performed, there were occurred pressure losses in the column on the 12th day after the start of the operation, and then the operation became difficult to continue. After stopped, when the interior of the column was inspected with his eyes, there was found occurrence of a lot of polymer.

EXAMPLE 3

Distillation Column for Separating High Boiling Point Materials

Distillation procedure for separating high boiling point materials from the acrylic acid solution was performed employing the same column as used in Example 1, except that the tube for feeding the raw material liquid was equipped to the bottom part thereof.

The raw material liquid contained a crude acrylic acid of 97 wt. % of acrylic acid, 0.03 wt. % of acetic acid, 0.02 wt. % of water, 0.5 wt. % of maleic acid, 0.001 wt. % of toluene, and 2.45 wt. % of the other residue, and was fed to the distillation column at a rate of 10 liter/hr. The crude acrylic acid was obtained from Example 1. In this case, the raw material liquid was maintained at a temperature of 75±3° C., and fed to the column. The operation conditions were as follows: operation pressure was 130 hPa, the bottom temperature 91° C., reflux liquid 13.7 liter/hr, the distilled 9.1 liter/hr, and the withdrawn 0.9 liter/hr.

A 10 ppm of copper dibutyldithiocarbamate and 100 ppm of methoquinone (each based on the amount of distilled acrylic acid) as the polymerization inhibitor each were dissolved into the reflux liquid, and then fed to the top part of the column. Furthermore, oxygen gas was fed to the bottom part thereof at 0.3 vol. % based on the amount of distilled acrylic acid.

The composition of distillate from the top in a steady state contained 99.9 wt. % of acrylic acid, 0.01 wt. % of water, less than 1 wt. ppm of maleic acid, and 0.09 wt. % of residue.

Continuous operation was steadily performed for 30 days under the above conditions. After stopped, when the interior of the column was inspected with his eyes, there was found no occurrence of polymer.

COMPARATIVE EXAMPLE 2

The procedure of Example 3 was repeated, except that the raw material liquid keeping a temperature of 25±3° C. was fed to the column.

Operation was continued for 30 days under the above conditions. After stopped, when the interior of the column was inspected with his eyes, there was found occurrence of a lot of polymer.

EXAMPLE 4

Aldehyde Separation Distillation Column

Continuous distillation was performed for the raw material liquid of the acrylic acid solution (acrylic acid concentration: 99.5 wt. %) including 450 wt. ppm of furfural, 50 wt. ppm of acrolein and 10 wt. ppm of toluene employing the same column as used in Example 1, except that the tube for feeding the raw material liquid was equipped to the bottom part thereof. To the raw material liquid, was added 500 wt. ppm of hydrazine hydrate (hydrazine 1 hydrate) based on the weight of the raw material liquid. An aldehyde treatment was performed in a retention vessel by the reaction of continuous withdrawn in order to make the retention time of the raw material liquid 15 minutes at normal temperature.

Then, aldehyde distillation was continuously operated while feeding the acrylic acid solution at a rate of 11 kg/hr., after aldehyde treatment, to the bottom part of the aldehyde distillation column. The operation conditions were as follows: operation pressure 55 hPa, the top temperature 60° C., the bottom temperature 63° C., reflux ratio 0.5, the distilled from the top part 10 kg/hr, and the withdrawn from the bottom 1 kg/hr. In this case, the raw material liquid keeping a temperature of 45±3° C. was fed to the column. Furthermore, in the case of distillation, 150 ppm of p-methoxyphenol, based on the weight of the raw material liquid, was added as the polymerization inhibitor to the reflux liquid, and oxygen gas was fed to the bottom part thereof at 0.3 vol. % based on the amount of distilled acrylic acid.

The resulting purified acrylic acid included 0.2 wt. ppm of furfural and less than 0.1 wt. ppm of acrolein.

Continuous operation was steadily performed for 30 days under the above conditions. After stopped, when the interior of the column was inspected with his eyes, there was found no occurrence of polymer.

COMPARATIVE EXAMPLE 3

The procedure of Example 4 was repeated, except that the raw material liquid was adjusted at a temperature of 20±3° C., and fed to the column.

When operation was performed, there were occurred pressure losses in the column on the 20th day after the start of the operation, and then the operation became difficult to continue. After stopped, when the interior of the column was inspected with his eyes, there was found occurrence of a lot of polymer.

EXAMPLE 5

Distillation Column for Separating High Boiling Point Materials

The procedure of Example 3 was repeated, except that continuous operation was set at 60 days.

Continuous operation was steadily performed for 60 days under the above conditions. After stopped, when the interior of the column was inspected with his eyes, there was found no occurrence of polymer.

COMPARATIVE EXAMPLE 4

The procedure of Example 3 was repeated, except that the raw material liquid was kept at a temperature of 25±3° C. and fed to the column.

When operation was performed, there were occurred pressure losses in the column on the 45th day after the start of the operation, and then the operation became difficult to continue. After stopped, when the interior of the column was inspected with his eyes, there was found occurrence of a lot of polymer.

EXAMPLE 6

The procedure of Example 1 was repeated, except that the raw material liquid was kept at a temperature of 50±1° C. and fed to the column.

Continuous operation was steadily performed for 30 days under the above conditions. After stopped, when the interior of the column was inspected with his eyes, there was found occurrence of little polymer.

COMPARATIVE EXAMPLE 5

The procedure of Example 1 was repeated, except that the raw material liquid was kept at a temperature of 40±1° C. and fed to the column.

When operation was performed, there were occurred pressure losses in the column on the 28th day after the start of the operation, and then the operation became difficult to continue. After stopped, when the interior of the column was inspected with his eyes, there was found occurrence of a lot of polymer.

COMPARATIVE EXAMPLE 6

The procedure of Example 1 was repeated, except that the raw material liquid was kept at the concentration of azeotropic agent being 10 wt. % and fed to the column.

When operation was performed, there were occurred pressure losses in the column on the 21st day after the start of the operation, and then the operation became difficult to continue. After stopped, when the interior of the column was inspected with his eyes, there was found occurrence of a lot of polymer.

The entire disclosure of Japanese Patent Application No. 2001-80075 filed on Mar. 21, 2001 including specification, claims and summary are incorporated herein by reference in its entirety.

What is claimed is:

1. A method for distilling a raw material liquid containing (meth)acrylic acid free from azeotropic solvents, which comprises;

subjecting gas phase catalytic oxidation reaction of propylene and/or acrolein with a molecular oxygen-containing gas or by gas phase catalytic oxidation reaction of at least one selected from the group consisting of isobutylene, t-butyl alcohol and methacrolein with the molecular oxygen-containing gas to form a mixed gas;

feeding the resulting mixed gas to a (meth)acrylic acid collection column wherein materials containing (meth)acrylic acid are collected with a collection agent to form the raw material liquid containing (meth)acrylic acid free from azeotropic solvents;

feeding to a distillation column the raw material liquid containing (meth)acrylic acid free from azeotropic solvents which temperature is substantially equal to that of an entrance place in the column; and distilling the raw material liquid in the distillation column, wherein the temperature of the raw material liquid is adjusted by heating or cooling.

2. A method according to claim 1, wherein the heating or cooling is performed by a heat exchanger.

3. A method according to claim 1, wherein the heating or cooling is performed based on the result that the temperature of the entrance place in the column is measured.

4. A method according to claim 1, wherein the distillation column is at least one selected from the group consisting of an aldehyde distillation column for the raw material liquid treated by an aldehyde treating agent and a distillation column for separating high boiling point materials for the raw material liquid.

5. A method for distilling a raw material liquid containing (meth)acrylic acid free from azeotropic solvents, which comprises;

subjecting gas phase catalytic oxidation reaction of propylene and/or acrolein with a molecular oxygen-containing gas or by gas phase catalytic oxidation reaction of at least one selected from the group consisting of isobutylene, t-butyl alcohol and methacrolein with the molecular oxygen-containing gas to form a mixed gas;

feeding the resulting mixed gas to a (meth)acrylic acid collection column wherein materials containing (meth)acrylic acid are collected with a collection agent to form the raw material liquid;

feeding to a distillation column the raw material liquid containing (meth)acrylic acid free from azeotropic solvents which temperature is substantially equal to that of an entrance place in the column; and distilling the raw material liquid in the distillation column, wherein the temperature of the raw material liquid to be fed (T0) and a temperature of the entrance place in the distillation column (T1) fulfill the following formula (1a):

$$0° C. \leq |T0-T1| \leq 30° C. \tag{1a}$$

6. A method according to claim 5, wherein the temperature of the raw material liquid to be fed (T0) and the temperature of the entrance place in the distillation column (T1) fulfill the following formula (1b):

$$0° C. \leq |T0-T1| \leq 20° C. \tag{1b}$$

7. A method according to claim 5, wherein the temperature of the raw material liquid to be fed (T0) and the temperature of the entrance place in the distillation column (T1) fulfill the following formula (1c):

$$0° C. \leq |T0T1| \leq 10° C. \tag{1c}$$

8. A method according to claim 5, wherein the temperature of the raw material liquid to be fed to the column is lower than that of a bottom part in the column.

9. A method according to claim 5, wherein the raw material liquid is divided into two or more separate streams, and then fed to the distillation column.

10. A method according to claim 5, wherein the collection agent is water or a process wastewater.

11. A method according to claim 10, wherein (meth)acrylic acid is recovered employing an azeotropic solvent to separate the collection agent therefrom.

12. A method according to claim 11, wherein the azeotropic solvent is at least one selected from the group consisting of diethyl ketone, methyl propyl ketone, methyl isobutyl ketone, methyl-t-butyl ketone, n-propyl acetate, toluene, heptane, and methylcyclohexane.

13. A method according to claim 5, wherein the distillation column is maintained under the following conditions:

Operation pressure: 10 to 400 hPa

Top temperature of the column: 45° C. to 110° C.

Temperature at which the raw material liquid is fed to the entrance place in the column: 40° C. to 120° C.

Bottom temperature: 50° C. to 190° C.

Reflux ratio: 0.1 to 5.

14. A method according to claim 5, wherein the distillation column is at least one selected from the group consisting of an aldehyde distillation column for the raw material liquid treated by an aldehyde treating agent and a distillation column for separating high boiling point materials for the raw material liquid.

15. A method for distilling a raw material liquid containing (meth)acrylic acid free from azeotropic solvents, which comprises;

subjecting gas phase catalytic oxidation reaction of propylene and/or acrolein with a molecular oxygen-containing gas or by gas phase catalytic oxidation reaction of at least one selected from the group consisting of isobutylene, t-butyl alcohol and methacrolein with the molecular oxygen-containing gas to form a mixed gas;

feeding the resulting mixed gas to a (meth)acrylic acid collection column wherein materials containing (meth)acrylic acid are collected with a collection agent to form the raw material liquid containing (meth)acrylic acid free from azeotropic solvents;

feeding to a distillation column the raw material liquid containing (meth)acrylic acid substantially free from azeotropic solvents which temperature is substantially equal to that of an entrance place in the column; and distilling the raw material liquid in the distillation column, wherein a fluctuation range (ΔT0) of temperature (T0) of the raw material liquid is within 10° C.

16. A method according to claim 15, wherein a fluctuation range (ΔT0) of temperature (T0) of the raw material liquid containing (meth)acrylic acid free from azeotropic solvents is within 50° C.

17. A method according to claim 15, wherein the fluctuation range (ΔT0) of temperature (T0) of the raw material liquid is within 30° C.

18. A method according to claim 15, wherein the distillation column is at least one selected from the group consisting of an aldehyde distillation column for the raw material liquid treated by an aldehyde treating agent and a distillation column for separating high boiling point materials for the raw material liquid.

* * * * *